United States Patent
Lenarz et al.

(10) Patent No.: US 6,377,849 B1
(45) Date of Patent: Apr. 23, 2002

(54) CATHETER FOR APPLYING MEDICATION INTO THE ENDOLYMPHATIC SACS OF THE COCHLEA

(76) Inventors: Thomas Lenarz, Aussiger Wende 7B; Ralf Heermann, Kleiner Hillen 7, both of D-30559 Hannover (DE)

( * ) Notice: Subject to any disclaimer, the term of this patent is extended or adjusted under 35 U.S.C. 154(b) by 0 days.

(21) Appl. No.: 09/443,534

(22) Filed: Nov. 19, 1999

(30) Foreign Application Priority Data

Nov. 19, 1998 (DE) .......................................... 198 53 299

(51) Int. Cl.⁷ ................................................ A61N 1/30
(52) U.S. Cl. ........................ 604/21; 604/174; 604/175; 604/912
(58) Field of Search ................................ 604/174, 175, 604/177, 264, 523, 908, 910, 912, 918, 21, 20

(56) References Cited

U.S. PATENT DOCUMENTS

| | | | | |
|---|---|---|---|---|
| 4,588,394 A | * | 5/1986 | Schulte et al. ................. | 604/9 |
| 4,915,694 A | * | 4/1990 | Yamamoto et al. .......... | 604/180 |
| 4,973,305 A | * | 11/1990 | Goltzer ......................... | 604/51 |
| 5,195,526 A | | 3/1993 | Michelson | |
| 5,246,014 A | * | 9/1993 | Williams et al. ............. | 607/122 |
| 5,458,573 A | * | 10/1995 | Summers ..................... | 604/101 |
| 5,462,561 A | * | 10/1995 | Voda ........................... | 606/144 |
| 5,476,446 A | | 12/1995 | Arenburg | |
| 5,527,280 A | * | 6/1996 | Goelz ........................... | 604/96 |
| 5,713,847 A | | 2/1998 | Howard, III et al. | |
| 5,776,111 A | * | 7/1998 | Tesio ........................... | 604/264 |
| 5,897,531 A | * | 4/1999 | Amirana ...................... | 604/180 |
| 5,928,229 A | * | 7/1999 | Gough et al. ................. | 606/41 |

FOREIGN PATENT DOCUMENTS

| | | |
|---|---|---|
| DE | 87 07 762.0 | 8/1988 |
| WO | WO 95/20409 | 8/1995 |

* cited by examiner

*Primary Examiner*—Sharon Kennedy
*Assistant Examiner*—Kevin C. Sirmons
(74) *Attorney, Agent, or Firm*—Collard & Roe, P.C.

(57) ABSTRACT

A catheter for administering medication into the endolymphatic sacs of the cochlea of the inner ear in humans, through at least one membrane of the inner ear. The catheter is designed with at least one outflow aperture at one end for the medication being administered and with an anchoring element. A medication dosage system can be connected to the other end of the catheter. The outflow aperture can be fed through the membrane of the inner ear and the anchoring element is designed so that it can anchor itself against this membrane.

5 Claims, 6 Drawing Sheets

CATHETER FOR APPLYING MEDICATION INTO THE ENDOLYMPHATIC SACS OF THE COCHLEA

BACKGROUND OF THE INVENTION

The invention concerns a catheter for administering medication into the endolymphatic sacs of the inner ear in humans, through at least one membrane of the inner ear. The catheter has at least one outflow aperture at one end for the medication being administered. There is an anchoring element for the catheter at this end to anchor the catheter to the membrane. There is also a medication dosage system connected to the other end of the catheter.

THE PRIOR ART

This kind of catheter is used to administer medication into the endolymphatic sacs of the inner ear. Administration of medication to the inner ear is sometimes necessary to combat ear diseases and for balance. In particular, it is used for treating symptoms such as loss of hearing, vertigo or ringing in the ears (tinnitus). Tinnitus is described as the awareness of sound, such as ringing or whistling, within the inner ear without there actually being any external sound source.

The reasons for the emergence of these noises, only audible to the patient, are numerous, and the pathogenesis of such has not been clearly explained to date. Due to the difficulty in accessing the inner ear to treat the respective illnesses, the administration of medication has been standard. It has not been possible to effectively treat diseases of the inner ear, or treatment has only been performed with difficulty, due to the side effects of medication. Nowadays, treatment for hearing loss in the inner ear, vertigo or tinnitus is performed by vasoactive infusions, steroids or hyperbaric oxygen therapy. Anaesthetics and antidepressants are also used along with physical, surgical and psychotherapeutic measures.

Systemically administered medication not only affects the area of the inner ear but also the whole body. Side effects thereby occur even with minimal dosage, which makes specific therapy of the disorder of the inner ear impossible. The result of this is that the majority of patients today cannot be effectively treated. Physical, psychotherapeutic and surgical measures can only help in a very small percentage of cases.

Meaningful and effective therapy to the inner ear can only be achieved with a localized dose of drugs or by electrically induced stimuli. However, specific application of drugs has always posed problems.

In one known procedure, medication is administered via a tympanic tube in the middle ear with subsequent uncontrolled diffusion into the inner ear via the round window membrane. With this type of known procedure, the only medication that can be applied is that which is also diffusible, which is not the case with some types of medication. In addition, it is virtually impossible to determine, predict and monitor the diffusion rate of diffusible substances. Therefore, the amount of medication selected must err on the high side, so that an adequate amount of the applied substance per diffusion can reach the inner ear.

A generically known catheter, such as that produced by Neuro-Biometrix USA (now called Intra Ear) distributed under its trading name "Round Window µ Cath" and "Round Window E Cath", has a somewhat spherical flexible end portion, which is clamped into the niche of the membrane of the round window and anchors itself there. This ending has several apertures, from which the medication can be discharged and diffuses right through the membrane of the round window. These outflow apertures are spaced at a distance from the membrane of the round window. However this known catheter can only apply diffusible medication, as these substances must be able to diffuse right through the membrane of the round window.

It would be desirable to have a controllable direct administration of medication into the lymph filled compartments of the cochlea, as only then is specific therapy of the symptoms of the disease possible. Since the lymphatic fluid in the cochlea directly bathes the sensory cells requiring therapy, as a blood supply for the sensory cells is not however immediately available, it is therefore not possible to administer medication via the bloodstream directly to the location of the damaged cells. Therefore, the ability to control the direct administration of medication into the inner ear fluids is desired. Until now, only the following substances and methods have been available: steroids and osmotically effective substances, tinnitus suppressant medications from the group of membrane-effective drugs and transmitter substances, neurotrophine (i.e., substances that facilitate regeneration or protection of damaged inner ear auditory cells and attacked aural nerve tissues), antioxidants, gene therapy, the application of electrically charged particles for the treatment of tinnitus and ototoxic medication for eliminating equilibrium sensitive cells.

SUMMARY OF THE INVENTION

It is therefore an object of this invention to design a catheter of the kind mentioned previously, so that it facilitates direct application of medication into the inner ear, and which also offers safe and secure anchoring in the inner ear.

It is another object of the invention to provide a catheter that will not negatively affect the auditory performance of the patient and which can be removed again without any problems, once therapy is complete.

These and other objects are achieved by way of a catheter according to the invention having at least one outflow aperture at one end for the medication being administered and with an anchoring element. A medication dosage system can be connected to the other end of the catheter. The outflow aperture can be fed through the membrane of the inner ear, and the anchoring element is designed so that it can anchor itself against this membrane.

The invention envisages a catheter of the type mentioned above, designed so that the outflow aperture can be fed through the tympanic membrane and the anchoring element anchors itself directly against the membrane.

A catheter of this kind can be created in a surprisingly simple manner to facilitate the direct application of medication into the inner ear and provide safe and durable anchoring within the inner ear. The catheter is designed so that it can be affixed to the round window membrane, to the base of the stapes at the oval window, or to the membrane of the endolymphatic sac, and the medication is then fed into the compartment behind the membrane.

The catheter according to the invention can also be combined with a medication dosage system, particularly one for micro-dosage system.

Depending upon whether the catheter according to the invention is to be anchored at the round window membrane, to the base of the stapes at the oval window, to the membrane of the endolymphatic sac or to the bone between the scala tympani and the cochlea duct, a posterior tympanotomy (starting at the drilled tympanic membrane) is well suited as the access route to these membranes for access to the round and oval windows, and the transmeatal access route (via the auditory canal) is also suitable for positioning the catheter according to the invention. A combined access route can offer additional advantages where appropriate. The catheter for the endolymphatic sac can be anchored within the parameters of a mastoidectomy (starting at the drilled tympanic membrane) and then exposing the sac in the area of the sigmoid sinus. A diagonal incision in the area of the upper and lateral sections is made. The catheter (depending on the size of the system) is fed into the opening and anchors itself.

The configuration of the elements facilitates adequate sealing of the exposed cochlear duct. The connective tissue membrane offers additional security. Due to the flexible nature of the suspending catheter at the respective membrane, deterioration of auditory performance is not expected. Removal of the catheter can be performed without damage, and closure of the lumens can be achieved with connective tissue or similar tissue. A measuring instrument or other instruments make the selection of size, positioning, and fixing of the catheter very simple. It is possible to integrate a wide variety of sensors and electrodes into the catheter. It is also possible to design the catheter extremity with various coupling elements to facilitate the attachment of a micro-dosage system.

Another advantage of the catheter according to the present invention is that it can be easily removed upon completion of therapy. Upon removal of the catheter, the aperture left behind in the corresponding membrane can be covered and closed up initially with grafted tissue, so that fluid cannot flow through the opening out of the inner ear. Subsequently, the scar tissue heals as a natural process, whereupon the aperture completely closes up. This scar tissue does not affect auditory performance.

In a preferred embodiment of the invention, one end is designed with a disc arranged across and encompassing the catheter tube for anchoring it to the round window membrane (or for anchoring it to the basilar membrane) and having a cannula point with an outflow aperture, which can be fed through the membrane. The disc has at least one anchoring element on its edge, which is designed to anchor against the osseous border of the round window (or the basilar membrane). The cannula point can be combined with an electro-conductive cable and may be made of a metallic material. The disc can have a diameter of between 0.7 mm and 1.2 mm.

This catheter can take advantage of the anatomical geometry of the round window and its membrane in a surprisingly simple way. Then with the cannula point, disc and anchoring stays, it is only necessary to pierce through the membrane of the round window with the cannula point, after which the anchoring stay or stays snap into the osseous border of the round window. This is because this osseous border of the round window already has overhanging edges that are well suited for positioning the anchoring elements.

In another embodiment of the invention, one end of the catheter has a bulbous extension, the end wall of which has an outflow aperture and at least two anchoring stays made of a flexible material having memory and arranged concentrically around the outflow aperture. The anchoring stays can be fed through the footplate of the stapes at the oval window and anchor themselves against the inner surface of the footplate. In further embodiments of this configuration, the bulbous extension is fitted with a clip, which anchors itself against the base of stapes. Another configuration has the catheter, the bulbous extension, and the stays enveloped in a removable tube, which has an internal diameter corresponding to the outer diameter of the bulbous extension.

This embodiment of the catheter is very suitable for attachment to the footplate of the stapes at the oval window. Also, attachment of the catheter to the footplate is performed in a conceivably simple manner. First, an aperture is made in the footplate of the oval window. Then, the catheter with its bulbous extension is anchored at the footplate of the oval window so that the anchoring elements are fed through the aperture in the footplate.

Due to the memory characteristics of the material of the anchoring stays, they flex themselves outwards after they have been inserted, by way of which the catheter is thereby anchored. The optional enveloping tube extends the anchoring stays in an axial direction and anchors the bulbous extension to the footplate of the oval window using anchoring stays, and the anchoring stays are fed through the opening in the footplate. As soon as the anchoring stays have been fed through the footplate and have left the rigid mantle of the enveloping tube, the anchoring stays flex according to the memory characteristic of the material and anchor themselves against the inner surface of the footplate. Subsequently, the enveloping tube can be pulled out towards the rear and removed. It is possible to remove the catheter by pulling it, because the metal has the property of memory and has a flectional resistance lower than the tensile resistance of the footplate.

In a third embodiment of the invention, one end of the catheter is fitted with a conical body having a front outflow aperture, whose minimum diameter is greater than the diameter of the catheter tube. The body is fitted with at least two hook-like anchoring elements bent backwards to its outer mantle, which together with a front sub-section of the conical body can be fed through the membrane of the endolymphatic sac, and anchor themselves against the inner surface of the membrane of the endolymphatic sac.

It is also easy to feed this kind of catheter through the membrane of the endolymphatic sac and to anchor it against the membrane of the endolymphatic sac.

In accordance with practical embodiments of the invention, the coupling elements of the catheter are made of carbon material or titanium oxide ceramic. The other parts of the catheter can be made of silicon. These materials have proven to be particularly suitable for implantation into the human body without affecting the surrounding tissue.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 6:
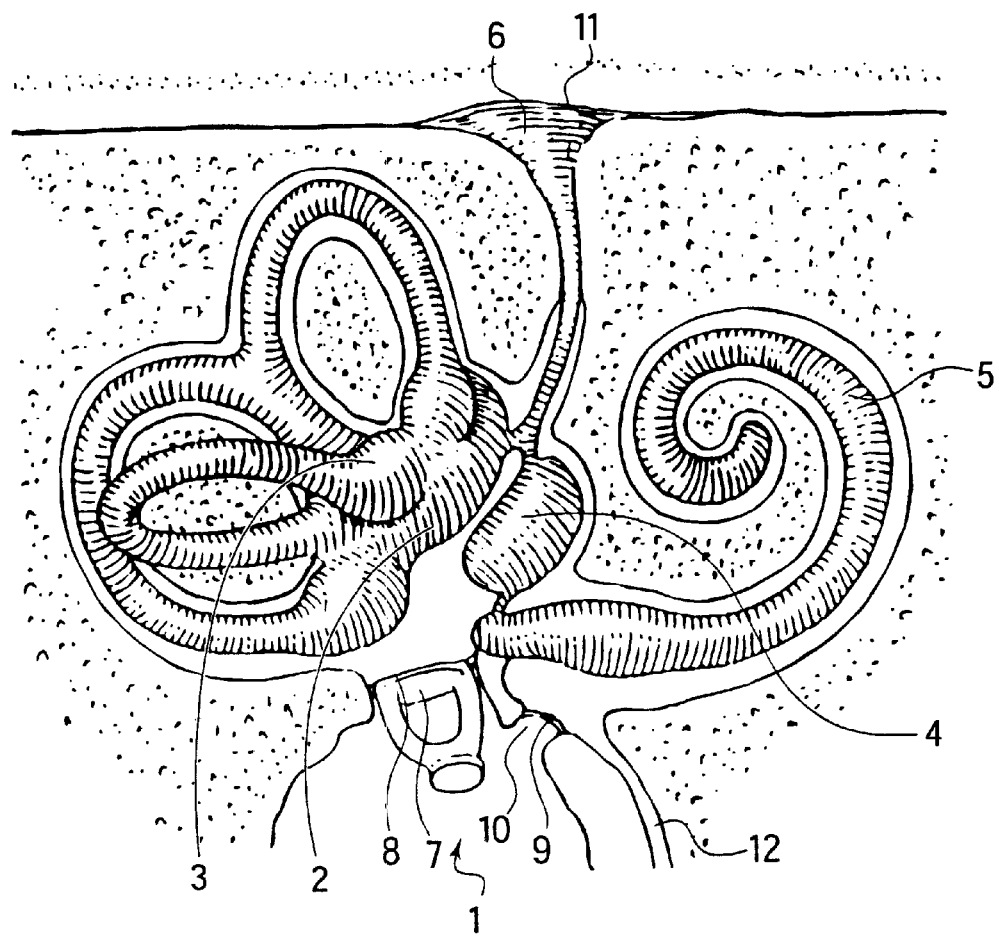
FIG. 6 shows an enlarged perspective of the anatomical features of the human inner ear.

Referring now in detail to the drawings, the geometry of the human inner ear 1 is explained, using FIG. 6 as an example. Ear 1 comprises the utricle 2, the ampulla of the lateral semicircular canal 3, the saccule 4, the cochlear duct 5 and the endolymphatic sac 6. The inner ear 1 is particularly demarcated by the footplate 7 of the stapes at the oval window 8, by the membrane 9 of the round window 10 and by the membrane 11 of the endolymphatic sac 6. An additional access route to the inner ear is provided by the auditory tube 12.

For physiological reasons, the footplate 7 of the oval window 8, the membrane 9 of the round window 10 as well as the membrane 11 of the endolymphatic sac 6 are suitable for applying medication to the inner ear 1. Also suitable is the basilar membrane which is not depicted in FIG. 6, if an operation similar to the Cochlear Implant Operation is going to be performed.

Figure 1:
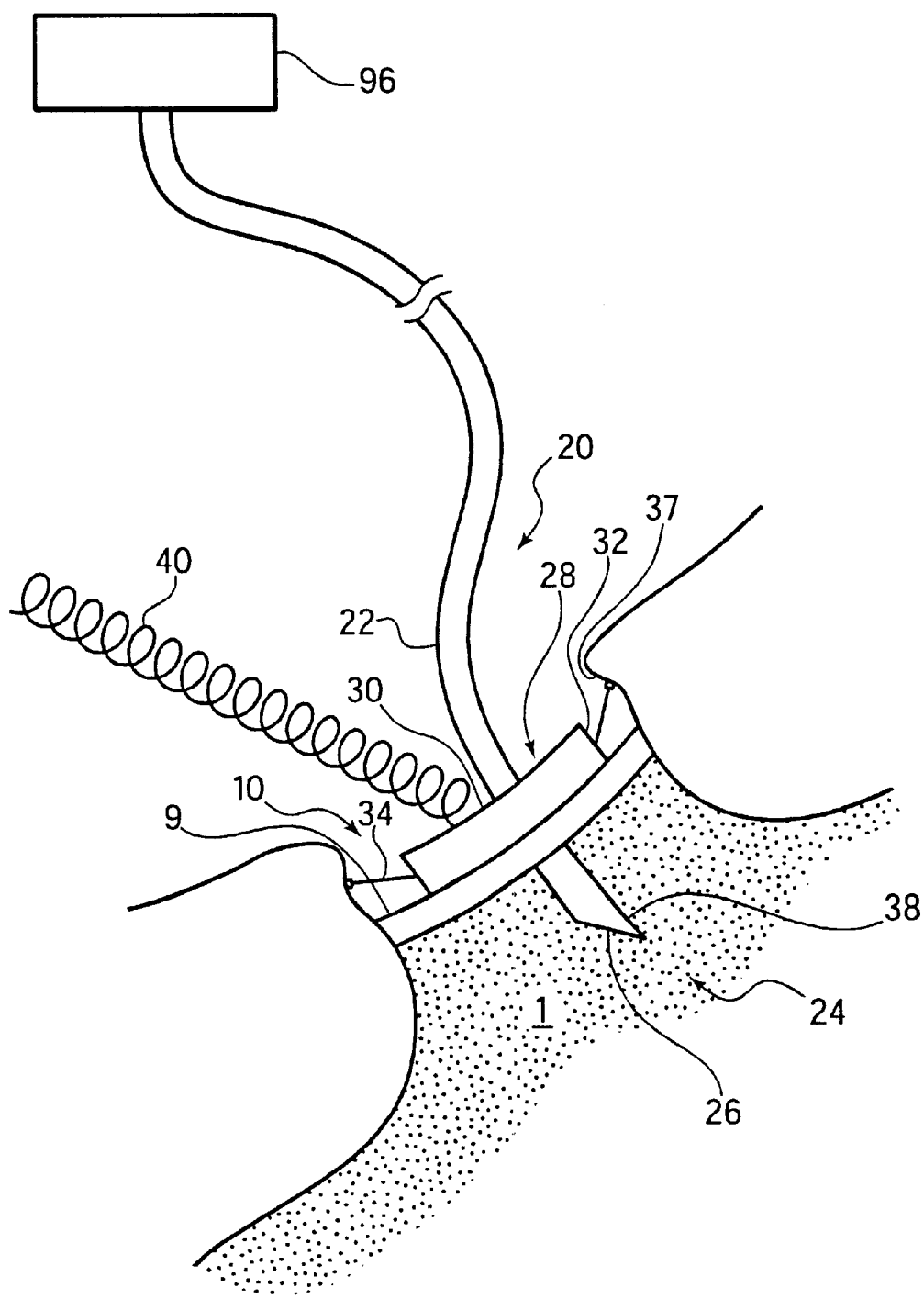
FIG. 1 shows a side view of a first embodiment of a catheter according to the invention.

FIG. 1 depicts a first embodiment of a catheter 20 according to the invention. Catheter 20 is fitted with a catheter tube 22, only a section of which is depicted in FIG. 1. At the one end 24, the catheter 20 is fitted with an outflow aperture 26. It is through this outflow aperture 26 that the medication fed through the catheter tube 26 can leave the catheter 20 and discharge into the inner ear 1. Catheter 20 can also be combined with a medication dosage system 96, particularly one for micro-dosage system.

At the end 24 of catheter 20, an anchoring element 28 is arranged for anchoring catheter 20 to membrane 9 of round window 10. Anchoring element 28 comprises a disc 30, which is arranged across and encompassing catheter tube 22 and which is in contact with membrane 9. Disc 30 is designed with two anchoring stays 34, 36 on its edge, which anchor themselves against overhanging osseous border 37 of round window 10.

The one end 24 with outflow aperture 26 has a cannula point 38. Cannula point 38 can be made of metallic material, for example V4A steel or titanium, and is connected to an electro-conductive cable 40 as indicated in FIG. 1. Cable 40 can be used for applying electrically induced stimulations to inner ear 1, or for recovering electric responses from the inner ear.

Disc 30 can be made of silicon and can have a diameter of 0.7, 1.2, or 1.7 mm with a thickness of 0.2 mm. Cannula point 38 preferably has a diameter of 0.3 mm and a length of 0.5 mm. Catheter tube 22 has an internal diameter of 0.3 mm, an outer diameter of 0.7 mm and a length of up to approximately 200 mm, and can be connected to dosage system 96 still to be described. Anchoring stays 34, 36 at edge 32 of disc 30 can be between 0.7 and 1.0 mm long.

Catheter 20 depicted in FIG. 1 can be attached at a cochleostomy, i.e., at an artificially created aperture in the inner ear. Here the bone of the spiral organ/cochlea is removed using a drill and the inner bone membrane, the so called scala timpani, is exposed across a large enough surface, about 2×2 mm in size. The scala timpani is a connective tissue membrane, which surrounds the perilymph as the innermost layer. After exposure, similar to the membrane 9 of round window 10, it can be punctured and disc 30 with anchoring elements 34, 36 can be anchored at the surrounding osseous border.

Disc 30 also prevents cannula point 38 from penetrating too far into inner ear 1 and in so doing guarantees a maximum depth of insertion. At the same time, disc 30 acts as a sealing element at the inner ear 1 side. The maximum guaranteed depth of penetration prevents damage to the basilar membrane or to other intracochlear structures. Due to the minimal depth of insertion, development of foreign body reactions and/or direct mechanical damage can be avoided or at least considerably reduced.

Figure 2:
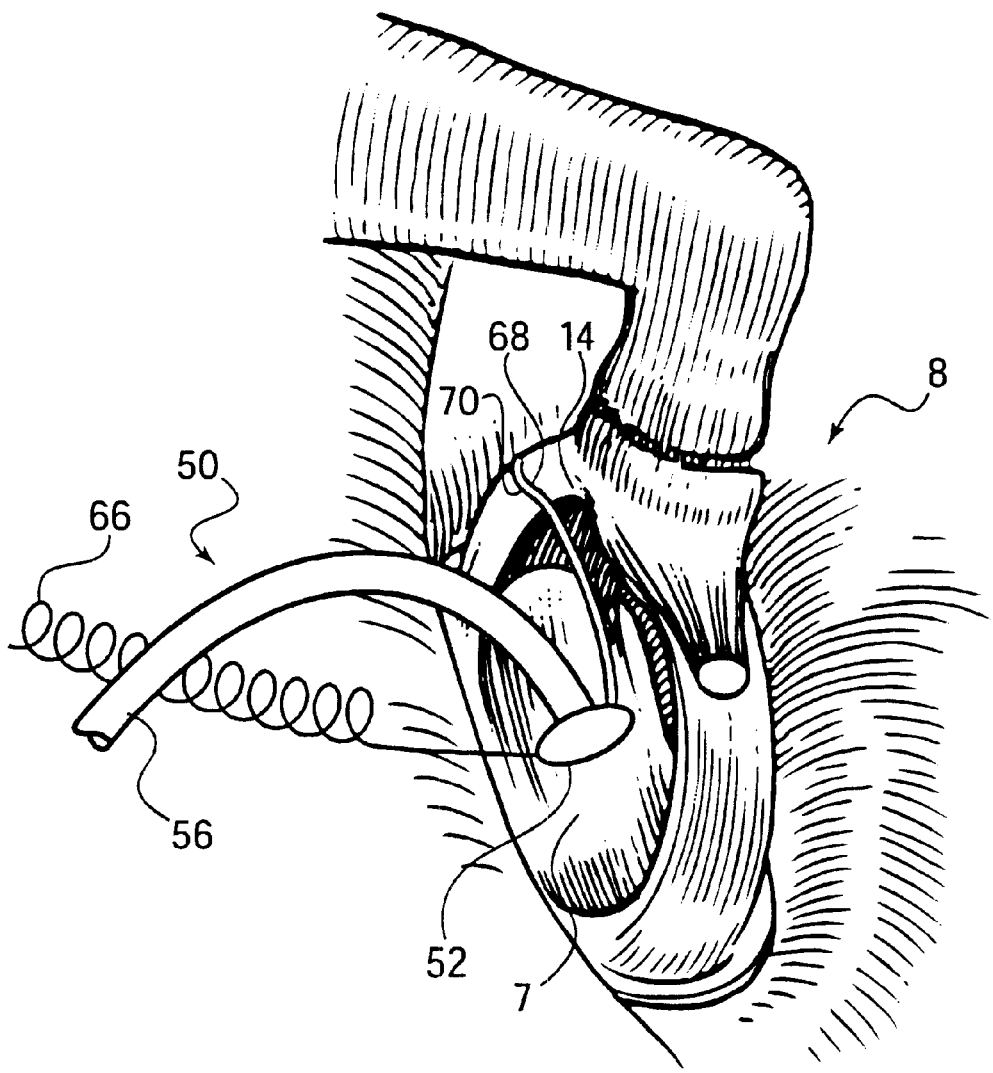
FIG. 2 shows a perspective view of a second embodiment of the catheter according to the invention.
Figure 3:
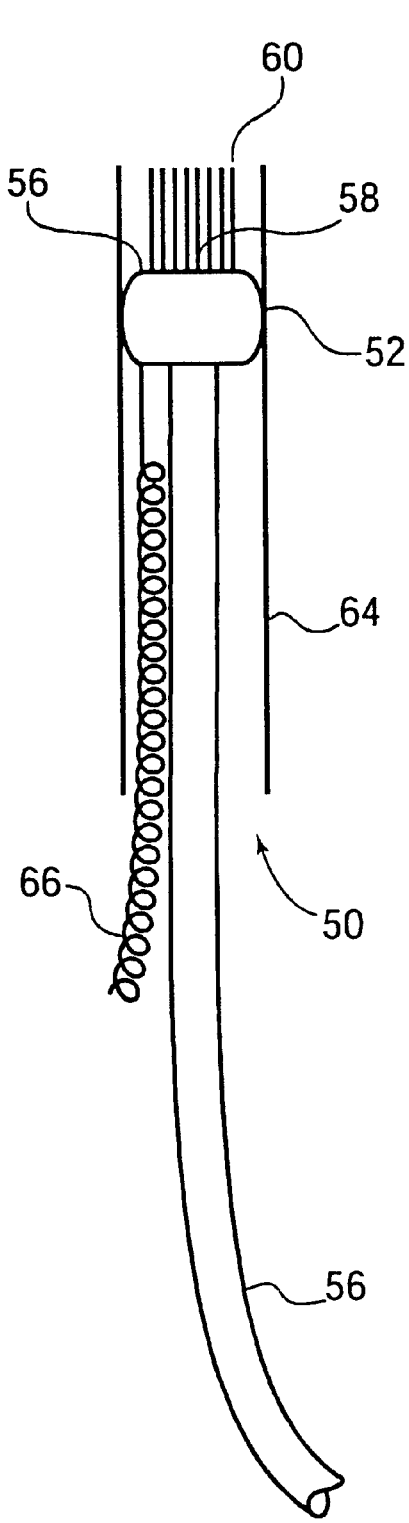
FIGS. 3 and 4 show a side view of a detail of the catheter shown in FIG. 2.
Figure 4:
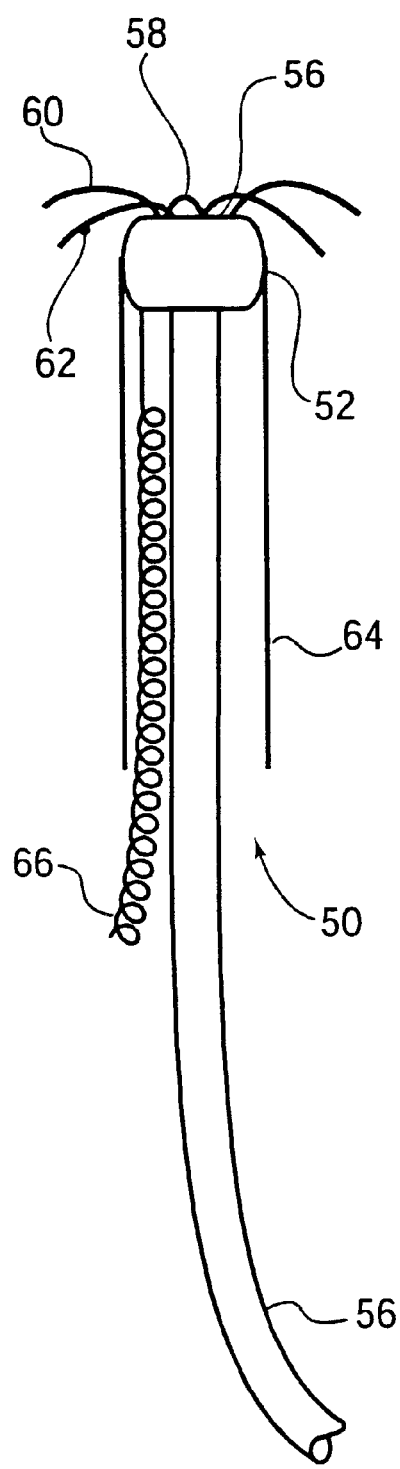

In FIGS. 2–4, the second embodiment of catheter 50 is depicted according to the invention. This catheter 50 has a bulbous extension 52, which is arranged at the end 54 of the catheter 50. Catheter 50 also has a catheter tube 56, only a section of which is shown in FIGS. 2–4.

One outflow aperture 58 is arranged centrally at the one end surface 56 of the bulbous extension 52, through which medication applied into catheter 50 can be discharged. Several anchoring elements 60 in the form of anchoring stays 62 made of a material having memory are arranged concentrically around the outflow aperture 58 of bulbous extension 56. These stays are designed so that after being extended they spring back into their original position, as shown in FIG. 4.

In order to be able to anchor catheter 50 into position at footplate 7 of oval window 8 as shown in FIG. 2, footplate 7 is pierced, then anchoring stays 62 are fed through this aperture in footplate 7, after which they anchor themselves against the inside of the footplate 7. In order to ease insertion of front end 54 of catheter 50, an enveloping tube 64 can be used, which is indicated in FIGS. 3 and 4. As shown in FIG. 3 the enveloping tube 64 covers the bulbous extension 52 and the anchoring stays 62, so that they can be extended axially forward.

If catheter 50 is placed at the opening of footplate 7 in this way, then catheter 50 can be pushed forward toward the inner ear. As soon as anchoring stays 62 have passed through the opening at footplate 7 and emerge away from the area influenced by the enveloping tube 64, they spring back due to their memory and anchor themselves at the inside of footplate 7. After that, enveloping tube 64 can be removed by pulling it out backwards.

Bulbous extension 52 can be made of silicon or from a related material and has a diameter of 1 mm and a thickness of 0.6 mm. The inner lumen of bulbous extension 52 can correspond to the inner lumen of catheter tube 52, i.e., approximately 0.4 mm.

Similar to catheter 20 in FIG. 1, catheter 50 can be fitted with a cable 66, which ends directly at the end surface 56 of bulbous extension 52, or it can be connected to an anchoring element 62, if this is made of metallic material.

As shown in FIG. 2, bulbous extension 52 is fitted with a clip 68, which can be made of platinum for example, and which anchors itself at end 70 against one of the crura of the base of the stapes 14.

Figure 5:
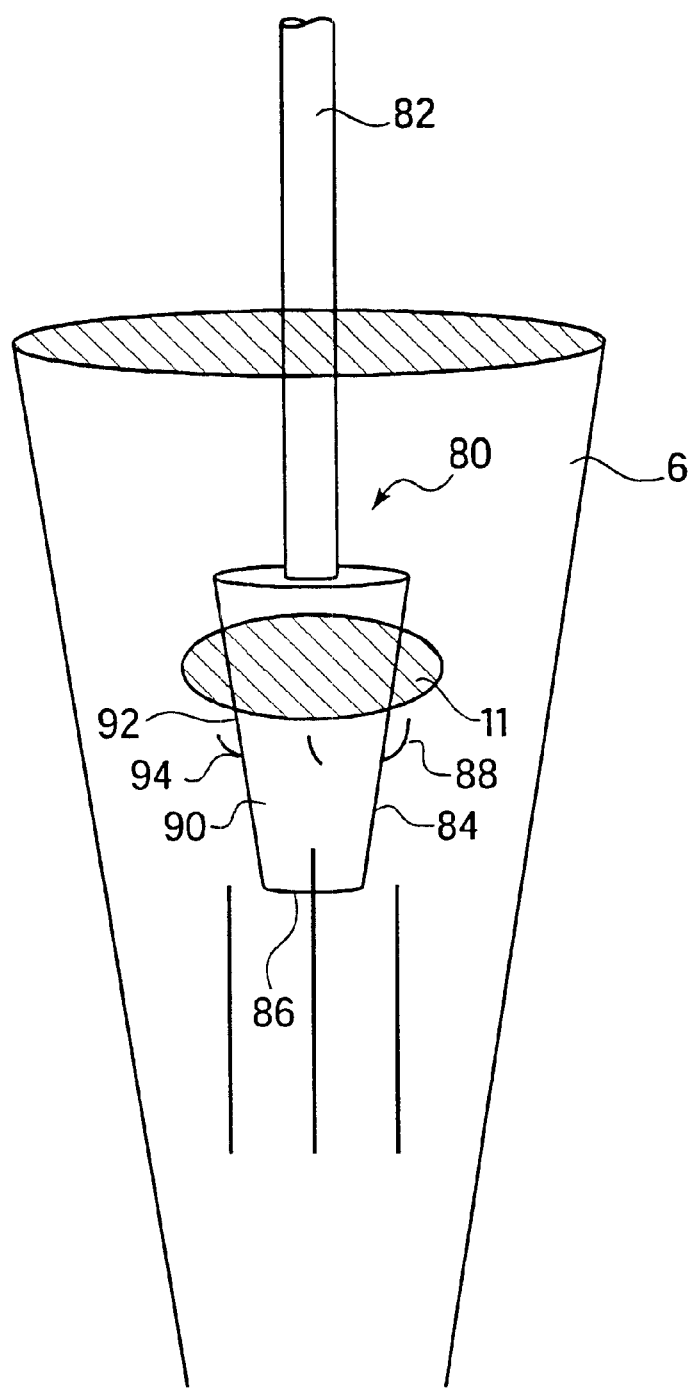
FIG. 5 shows a schematic view of a third embodiment of the catheter according to the invention.

A third embodiment of a catheter 80 according to the invention is schematically depicted in FIG. 5. Catheter 80 is fed into the endolymphatic sac 6 through membrane 11 of endolymphatic sac 6. Catheter 80 has a catheter tube 82, of which only a section is depicted in FIG. 5, as well as an end 84 with outflow aperture 86. Catheter 80 is also fitted with an anchoring element 88. Catheter 80 is designed with end 84 as a conical body 90, which has a minimum diameter greater than the diameter of catheter tube 82.

Hook-like anchoring stays 94 acting as anchoring elements 88 are attached to the mantle surface 92. These hooks are flexed with their ends toward the inner surface of membrane 11, so that after insertion into the aperture in the membrane 11, conical body 90 can be pushed through with hook-like anchoring elements 94 at least part way through the aperture in the membrane 11. This prevents conical body 90 from slipping out from the aperture in membrane 11 by hook-like anchoring elements 94. Anchoring elements 94 are made of silicon like body 90. In the embodiment shown, they have a length of 0.3 mm and a diameter of 0.1 mm.

Figure 7:
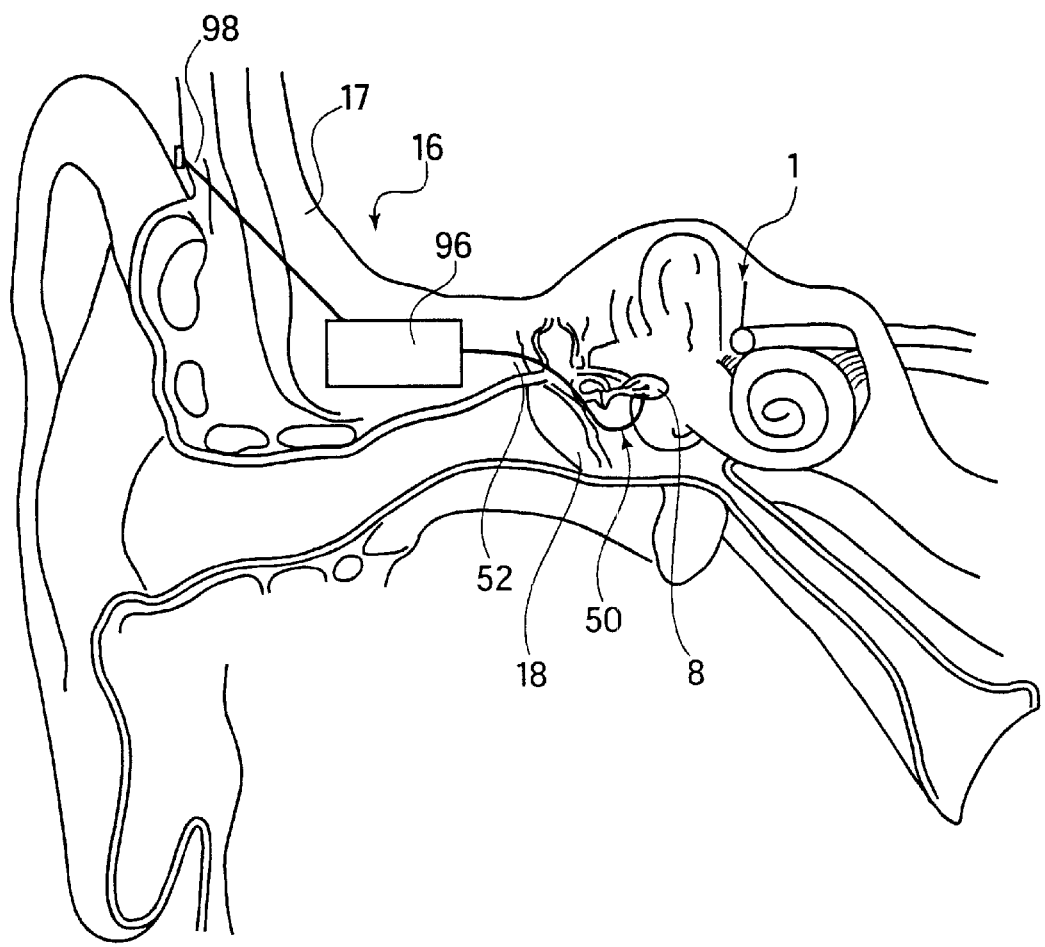
FIG. 7 shows a schematic view of a micro-dosage system used in conjunction with the catheter shown in FIGS. 2 to 4, in position in the human ear.

FIG. 7 schematically depicts the human ear 16 with the eardrum 18, which is fitted with a catheter 50 as shown in FIGS. 2–4. A catheter tube 52 is connected to a micro-dosage system 96, which can be implanted into the bony tissue 17 of ear 16. Catheter tube 52 passes through the middle ear. Catheter 50 is connected to the oval window 8 as shown in FIGS. 2–4.

The micro-dosage system 96 can have a drug reservoir, a micro-pump and an IC control, none of which are depicted. This releases a programmed amount of medication via catheter tube 52 into the inner ear 1. Micro-dosage system 96 also has a tube 98 emerging at the body outer mantle, through which medication can be supplied to the micro-dosage system 96. It is also possible for the medication to be transcutaneously fed into micro-dosage system 96 via a syringe.

Accordingly, while only a few embodiments of the present invention have been shown and described, it is obvious that many changes and modifications may be made thereunto without departing from the spirit and scope of the invention.

What is claimed is:

1. A catheter for administering medication into the endolymphatic sacs of an inner ear in humans through at least one membrane of the inner ear, the membranes comprising a membrane of a round window, a membrane of the endolymphatic sac and a basilar membrane, and an inner ear further having a stapes footplate, and a scala tympani with an osseous border, comprising:

a catheter tube having a first and a second end;

at least one outflow aperture at said first end of said catheter tube for administration of the medication through one of the membranes of the inner ear;

an anchoring element at said first end for anchoring said catheter directly against the membrane; and a medication dosage system connected to said second end of said catheter;

wherein said anchoring element comprises a disc arranged across and encompassing said catheter tube for anchoring said catheter tube, said disc covering the round window of the inner ear and having at least one anchoring stay on an edge, said stay anchoring against an osseous border of the round window, and further comprising a cannula point at said outflow aperture, said cannula point being feedable through said membrane.

2. A catheter according to claim 1, wherein the anchoring element comprises a disc arranged across and encompassing said catheter tube for anchoring said catheter tube to the basilar membrane, said disc having at least one anchoring stay at an edge, said stay anchoring against the osseous border of the scala tympani, and further comprising a cannula point at said outflow aperture, said cannula point being feedable through the scala tympani.

3. A catheter according to claim 1, further comprising an electro-conductive cable connected to said cannula point.

4. A catheter according to claim 1, wherein said disc has a diameter of 0.7 mm to 1.2 mm.

5. A catheter according to claim 1, wherein said cannula point is made of a metallic material.

\* \* \* \* \*